US006399573B1

(12) United States Patent
Young

(10) Patent No.: US 6,399,573 B1
(45) Date of Patent: Jun. 4, 2002

(54) INTERLEUKIN-1 RECEPTOR ANTAGONIST BETA (IL-1RABETA)

(75) Inventor: Peter Ronald Young, Laurenceville, NJ (US)

(73) Assignee: SmithKline Beecham Corporation, Philadelphia, PA (US)

(*) Notice: Subject to any disclaimer, the term of this patent is extended or adjusted under 35 U.S.C. 154(b) by 0 days.

(21) Appl. No.: 09/494,018

(22) Filed: Jan. 28, 2000

Related U.S. Application Data

(60) Division of application No. 09/069,619, filed on Apr. 29, 1998, which is a continuation-in-part of application No. 09/007,464, filed on Jan. 14, 1998, now abandoned, which is a continuation-in-part of application No. 08/790,032, filed on Jan. 28, 1997, now Pat. No. 5,863,769.

(51) Int. Cl.$^7$ .................. A61K 38/00; A61K 45/00; C07K 17/00
(52) U.S. Cl. ..................... 514/12; 514/2; 424/85.2; 530/351
(58) Field of Search ................. 530/351; 424/85.2; 514/2, 12

(56) References Cited

U.S. PATENT DOCUMENTS

| 5,075,222 A | 12/1991 | Hannum et al. ........... 435/69.1 |
| 5,455,330 A | 10/1995 | Haskill et al. .............. 530/350 |
| 5,863,769 A | 1/1999 | Young |

FOREIGN PATENT DOCUMENTS

| WO | WO9609323 | 3/1996 |

OTHER PUBLICATIONS

GenBank Accession No. G10162.
GenBank Accession No. N59092.
GenBank Accession No. T25675.
Gu et al., "Activation of Interferon—? Inducing Factor Mediated by Interleukin–1β Converting Enzyme", Science, vol. 275, pp. 206–209 (1997).
Bazan et al., "A newly defined interleukin–1", Nature, vol. 379, p. 591 (1996).
Okamura et al., "Cloning of a new cytokine that induces IFN–? production by T cells", Nature, vol. 378, pp. 88–91 (1995).
Haskill et al., "cDNA cloning of an intracellular form of the human interleukin 1 receptor antagonist Associated with epithelium", Proc. Natl. Acad. Sci., vol. 88, pp. 3681–3685 (1991).
Hannum et al., "Interleukin–1 receptor antagonist activity of a human interleukin–1 inhibitor", Nature, vol. 343, pp. 336–340 (1990).
Carter et al., "Purification cloning, expression and biological characterization of an interleukin–1 receptor Antagonist Protein", Nature, vol. 344, pp. 633–638 (1990).
Eisenberg et al., "Primary Structure and Functional Expression from Complementary DNA of a Human Interleukin–1 Receptor Antagonist", Nature, vol. 343, pp. 341–346.
Auron et al., "Nucleotide Sequence of Human Monocyte Interleukin–1 Precursor cDNA", Proc. Natl. Acad. Sci. USA, vol. 81, pp. 7907–7911 (1984).
C. J. March et al., "Cloning sequence and expression of two distinct human interleukin–1 complementary DNAs", Nature, vol. 315, pp. 641–647 (1985).
Deepe G. S. et al. (1986), Modulation of Cellular Immune Responses in Mice with Disseminated histoplasmosis by Recombinant Interleukin–2. Infection and Immunity, vol. 53 No. 1, pp. 6–12.*
Berkman N. et al. (1995), Inhibition of Macrophage inflammatory Protein–1 alpha Expression by IL–10. J. of Immunology, vol. 155: pp. 4412–4418.*
Jackson R. J. et al. (2001), Expression of mouse Interleukin–4 by a Recombinant Ectromelia Virus Suppresses Cytolytic Lymphocyte Responses and Overcomes Genetic Resistance to Mouse. J. of Virology, vol. 75 No. 3, pp. 1205–1210.*

* cited by examiner

Primary Examiner—Jeffrey Stucker
Assistant Examiner—Jegatheesan Seharaseyon
(74) Attorney, Agent, or Firm—William T. Han; William T. King; Charles M. Kinzig

(57) ABSTRACT

IL-1ra beta polypeptides and polynucleotides and methods for producing such polypeptides by recombinant techniques are disclosed. Also disclosed are methods for utilizing IL-1ra beta polypeptides and polynucleotides in the design of protocols for the treatment of chronic and acute inflammation, septicemia, arthritis, inflammatory bowel disease, graft vs. host disease, autoimmunity, stroke, cardiac ischemia, acute respiratory disease syndrome (ARDS), psoriasis, restenosis, traumatic brain injury, AIDS, cachexia, allergy, parasite infection, allergic rhinitis, allergic asthma, atopic dermatitis, allergic inflammatory diseases, and delayed hypersensitivity, among others, and diagnostic assays for such conditions.

1 Claim, 1 Drawing Sheet

FIGURE 1. Nucleotide and Amino Acid sequence of IL-1ra beta (SEQ ID NOS: 1 and 2, respectively.)

SEQ ID NO. 1

```
   1 GGCACGAGCC ACGATTCAGT CCCCTGGACT GTAGATAAAG ACCCTTTCTT
  51 GCCAGGTGCT GAGACAACCA CACTATGAGA GGCACTCCAG GAGACGCTGA
 101 TGGTGGAGGA AGGGCCGTCT ATCAATCAAT GTGTAAACCT ATTACTGGGA
 151 CTATTAATGA TTTGAATCAG CAAGTGTGGA CCCTTCAGGG TCAGAACCTT
 201 GTGGCAGTTC CACGAAGTGA CAGTGTGACC CCAGTCACTG TTGCTGTTAT
 251 CACATGCAAG TATCCAGAGG CTCTTGAGCA AGGCAGAGGG GATCCCATTT
 301 ATTTGGGAAT CCAGAATCCA GAAATGTGTT TGTATTGTGA GAAGGTTGGA
 351 GAACAGCCCA CATTGCAGCT AAAAGAGCAG AAGATCATGG ATCTGTATGG
 401 CCAACCCGAG CCCGTGAAAC CCTTCCTTTT CTACCGTGCC AAGACTGGTA
 451 GGACCTCCAC CCTTGAGTCT GTGGCCTTCC CGGACTGGTT CATTGCCTCC
 501 TCCAAGAGAG ACCAGCCCAT CATTCTGACT TCAGAACTTG GAAGTCATA
 551 CAACACTGCC TTTGAATTAA ATATAAATGA CTGAACTCAG CCTAGAGGTG
 601 GCAGCTTGGT CTTTGTCTTA AAGTTTCTGG TTCCCAATGT GTTTTCGTCT
 651 ACATTTTCTT AGTGTCATTT TCACGCTGGT GCTGAGACAG GGGCAAGGCT
 701 GCTGTTATCA TCTCATTTTA TAATGAAGAA GAAGCAATTA CTTCATAGCA
 751 ACTGAAGAAC AGGATGTGGC CTCAGAAGCA GGAGAGCTGG GTGGTATAAG
 801 GCTGTCCTCT CAAGCTGGTG CTGTGTAGGC ACAAGGCAT CTGCATGAGT
 851 GACTTTAAGA CTCAAAGACC AAACACTGAG CTTTCTTCTA GGGGTGGGTA
 901 TGAAGATGCT TCAGAGCTCA TGCGCGTTAC CCACGATGGC ATGACTAGCA
 951 CAGAGCTGAT CTCTGTTTCT GTTTTGCTTT ATTCCCTCTT GGGATGATAT
1001 CATCCAGTCT TTATATGTTG CCAATATACC TCATTGTGTG TAATAGAACC
1051 TTCTTAGCAT TAAGACCTTG TAAACAAAAA TAATTCTTGT GTTAAGTTAA
1101 ATCATTTTTG TCCTAATTGT AATGTGTAAT CTTAAAGTTA AATAAACTTT
1151 GTGTATTTAT ATAATAAAAA AAAAAAAAAA AAA
```

SEQ ID NO. 2

```
   1 MRGTPGDADG GGRAVYQSMC KPITGTINDL NQQVWTLQGQ NLVAVPRSDS
  51 VTPVTVAVIT CKYPEALEQG RGDPIYLGIQ NPEMCLYCEK VGEQPTLQLK
 101 EQKIMDLYGQ PEPVKPFLFY RAKTGRTSTL ESVAFPDWFI ASSKRDQPII
 151 LTSELGKSYN TAFELNIND
```

INTERLEUKIN-1 RECEPTOR ANTAGONIST BETA (IL-1RABETA)

CROSS REFERENCE TO RELATED APPLICATION

This application is a division of U.S. application Ser. No. 09/069,619, filed Apr. 29, 1998, which is a continuation-in-part application to U.S. patent application Ser. No. 09/007,464 filed Jan. 14, 1998 now abandoned which is a continuation-in-part of Ser. No. 08/790,032 filed Jan. 28, 1997 now U.S. Pat. No. 5,863,769. The aforementioned applications are incorporated by reference in their entirety.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to Interleukin-1 family, hereinafter referred to as IL-1ra beta. The invention also relates to inhibiting or activating the action of such polynucleotides and polypeptides.

BACKGROUND OF THE INVENTION

Interleukin 1 refers to two proteins (IL1α and IL1β) which play a key role early in the inflammatory response [for a review see C. A. Dinarello, Blood, 87:2095–2147 (1996) and references therein]. Both proteins are made as 31 kDal intracellular precursor proteins which are cleaved upon secretion to yield mature carboxy-terminal 17 kDal fragments which are biologically active. In the case of IL-1β, this cleavage involves an intracellular cysteine protease, known as ICE, which is required to release the active fragment from the inactive precursor. The precursor of IL-1α is active.

These two proteins act by binding to cell surface receptors found on almost all cell types and triggering a range of responses either alone or in concert with other secreted factors. These range from effects on proliferation (eg of fibroblasts, T cells), apoptosis (eg A375 melanoma cells), cytokine induction (eg of TNF, IL, IL8), receptor activation (eg E-selectin), eicosanoid production (eg PGE2) and the secretion of degradative enzymes (eg collagenase). To achieve this, IL-1 activates transcription factors such as NF-κB and AP-1, Several of the activities of IL-1 action on target cells are believed to be mediated through activation of kinase cascades that have also been associated with cellular stresses, such as the stress activated MAP kinases JNK/SAPK and p38.

A third member of the IL-1 family was subsequently discovered which acts as a natural antagonist of IL-1α and IL-1β by binding to the IL-1 receptor but not transducing an intracellular signal or a biological response. The protein was called IL-1ra (for IL-1 receptor antagonist) or IRAP (for IL-1 receptor antagonist protein). At least three alternatively splice forms of IL-1ra exist: one encodes a secreted protein, and the other two encode intracellular proteins. The relative role of the three forms and reason for their different localization is not known. All three proteins, IL-1α, IL-1β and IL-1ra share approximately 25–30% amino acid identity and a similar three-dimensional structure consisting of twelve β-strands folded into a β-barrel, with an internal thrice repeated structural motif.

There are three known IL-1 receptor subunits. The active receptor complex consists of the type I receptor and IL1RAcP (for IL-1 accessory protein). The type I receptor is responsible for binding of the three ligands, and is able to do so in the absence of the IL1RAcP. However signal transduction requires interaction of IL-1α or β with the IL1RAcP. IL-1ra does not interact with the IL-1RAcP and hence cannot signal. A third receptor subunit, the type II receptor, binds IL-1α and IL-1β but cannot signal due to its lack of an intracellular domain. Rather it act as a decoy either in its membrane form or an antagonist in a cleaved secreted form, and hence inhibits IL-1 activity. It only weakly binds IL-1ra.

Many studies using IL-1ra, soluble IL-1R, derived from the extracellular domain of the type I IL-1R, antibodies to IL-1α or β and transgenic knockouts of these genes have shown conclusively that the IL-1s play a key role in a number of pathophysiologies (see C. A. Dinarello, Blood 87:2095–2147 (1996) for a review). For example, IL-1ra has been shown to be effective in animal models of septic shock, rheumatoid arthritis, graft versus host disease, stroke, cardiac ischemia, and is currently in clinical trials for some of these indications. Moreover, IL-1α and β have shown some potential as hematopoietic stem cell stimulators with potential as radio- and chemoprotectants.

More recently, a more distant member of the IL-1 family was identified. This protein, originally isolated through its ability to induce Interferon gamma in T cells and hence called Interferon gamma inducing factor (IGIF) [H. Okamura et al., Nature 378:88–91 (1995)], was subsequently shown to fold in a similar structure to the IL-1s and share weak amino acid identity [Bazan et al., Nature 379:591 (1996)]. The name IL-1γ was proposed. IGIF appears to play a direct role in the liver damage which occurs during toxic shock and is therefore like the other IL-1s in playing an early role in inflammatory and stressful conditions.

This indicates that these Interleukin-1s have an established, proven history as therapeutic targets. Clearly there is a need for identification and characterization of further members of Interleukin-1 family which can play a role in preventing, ameliorating or correcting dysfunctions or diseases, including, but not limited to, chronic and acute inflammation, septicemia, shock, arthritis, inflammatory bowel disease, graft vs. host disease, autoimmunity, stroke, cardiac ischemia, acute respiratory disease syndrome (ARDS), psoriasis, restenosis, traumatic brain injury, AIDS, cachexia, allergy, parasite infection, allergic rhinitis, allergic asthma, atopic dermatitis, allergic inflammatory diseases, and delayed hypersensitivity.

SUMMARY OF THE INVENTION

In one aspect, the invention relates to IL-1ra beta polypeptides and recombinant materials and methods for their production. Another aspect of the invention relates to methods for using such IL-1ra beta polypeptides and polynucleotides. Such uses include the treatment of chronic and acute inflammation, septicemia, arthritis, inflammatory bowel disease, graft vs. host disease, autoimmunity, stroke, shock, cardiac ischemia, acute respiratory disease syndrome (ARDS), psoriasis, restenosis, traumatic brain injury, AIDS, cachexia, allergy, parasite infection, allergic rhinitis, allergic asthma, atopic dermatitis, allergic inflammatory diseases, and delayed hypersensitivity,, among others. In still another aspect, the invention relates to methods to identify agonists and antagonists using the materials provided by the invention, and treating conditions associated with IL-1ra beta imbalance with the identified compounds. Yet another aspect of the invention relates to diagnostic assays for detecting diseases associated with inappropriate IL-1ra beta activity or levels.

BRIEF DESCRIPTION OF THE DRAWINGS

FIG. 1 shows the nucleotide and deduced amino acid sequence of human IL-1ra beta. SEQ ID NOS: 1 and 2.

DESCRIPTION OF THE INVENTION

Definitions

The following definitions are provided to facilitate understanding of certain terms used frequently herein.

"IL-1ra beta" refers generally to a polypeptide having the amino acid sequence set forth in SEQ ID NO:2 or an allelic variant thereof.

"IL-1ra beta activity or IL-1ra beta polypeptide activity" or "biological activity of the IL-1ra beta or IL-1ra beta polypeptide" refers to the metabolic or physiologic function of said IL-1ra beta including similar activities or improved activities or these activities with decreased undesirable side-effects. Also included are antigenic and immunogenic activities of said IL-1ra beta.

"IL-1ra beta polypeptides" refers to polypeptides with amino acid sequences sufficiently similar to IL-1ra beta sequences, preferably exhibiting at least one biological activity of the IL-1ra beta.

"IL-1ra beta gene" refers to a polynucleotide having the nucleotide sequence set forth in SEQ ID NO:1 or allelic variants thereof and/or their complements.

"IL-1ra beta polynucleotides" refers to polynucleotides containing a nucleotide sequence which encodes a IL-1ra beta polypeptide or fragment thereof, or a nucleotide sequence which has at least 80% identity to a nucleotide sequence encoding the polypeptide of SEQ ID NO:2 or the corresponding fragment thereof, or a nucleotide sequence which has sufficient 80% identity to a nucleotide sequence contained in SEQ ID NO:1 to hybridize under conditions useable for amplification or for use as a probe or marker.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM J. *Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Atschul, S., et al., NCBI NLM NIH Bethesda, Md. 20894; Altschul, S., et al., *J. Mol Biol* 215: 403–410 (1990). The well known Smith Waterman algorithm may also be used to determine identity.

Preferred parameters for polypeptide sequence comparison include the following:
1) Algorithm: Needleman and Wunsch, J. Mol Biol. 48: 443–453 (1970)
Comparison matrix: BLOSSUM62 from Hentikoff and Hentikoff, Proc. Natl. Acad. Sci. USA. 89:10915–10919 (1992)
Gap Penalty: 12
Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Preferred parameters for polynucleotide comparison include the following:
1) Algorithm: Needleman and Wunsch, J. Mol Biol. 48: 443–453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

By way of example, a polynucleotide sequence of the present invention may be identical to the reference sequence of SEQ ID NO:1, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in SEQ ID NO:1 by the numerical percent of the respective percent identity(divided by 100) and subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, and y is, for instance, 0.70 for 70%, 0.80 for 80%, 0.85 for 85%, 0.90 for 90%, 0.95 for 95%, etc., and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

Similarly, a polypeptide sequence of the present invention may be identical to the reference sequence of SEQ ID NO:2, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the numerical percent of the respective percent identity(divided by 100) and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is, for instance 0.70 for 70%, 0.80 for 80%, 0.85 for 85% etc., and wherein any non-integer product of $x_a$ and y is rounded down to the nearest integer prior to subtracting it from $x_a$.

Polypeptides of the Invention

The IL-1ra beta polypeptides of the present invention include the polypeptide of SEQ ID NO:2 (in particular the mature polypeptide) as well as IL-1ra beta polypeptides and which have at least 80% identity to the polypeptide of SEQ ID NO:2 or the relevant portion and more preferably at least 85% identity, and still more preferably at least 90% identity, and even still more preferably at least 95% identity to SEQ ID NO:2.

The IL-1ra beta polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Biologically active fragments of the IL-1ra beta polypeptides are also included in the invention. A fragment is a polypeptide having an amino acid sequence that entirely is the same as part, but not all, of the amino acid sequence of the aforementioned IL-1ra beta polypeptides. As with IL-1ra beta polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of IL-1ra beta polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of IL-1ra beta polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Biologically active fragments are those that mediate IL-1ra beta activity, including those with a similar activity or an improved activity, or with a decreased undesirable activity. Also included are those that are antigenic or immunogenic in an animal, especially in a human.

Thus, the polypeptides of the invention include polypeptides having an amino acid sequence at least identical to that of SEQ ID NO:2 or fragments thereof with at least 80% identity to the corresponding fragment of SEQ ID NO:2. Preferably, all of these polypeptides retain the biological activity of the IL-1ra beta, including antigenic activity. Included in this group are variants of the defined sequence and fragments. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The IL-1ra beta polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to isolated polynucleotides which encode the IL-1ra beta polypeptides and polynucleotides closely related thereto.

IL-1ra beta of the invention is structurally related to other proteins of the Interleukin-1 family, as shown by the results of sequencing the cDNA encoding human IL-1ra beta. The cDNA sequence contains an open reading frame encoding a protein of 169 amino acids with a deduced molecular weight of 18.7 kDa. IL-1ra beta of FIG. 1 (SEQ ID NO:2) has about 29.9% identity (using BESTFIT (part of GCG suite of programs)) in amino acid residues with human IL-1 receptor antagonist (IL-1ra) (S. P. Eisenberg et al., Nature 343:341–346, 1990) over 162 residues. Furthermore, IL-1ra beta (SEQ ID NO:2) is 21.3% identical to human Interleukin 1 beta (IL-1beta) over 160 residues (P. E. Auron et al., Proc Natl. Acad. Sci. USA 81:7907–7911, 1984; C. J. March et al., Nature 315:641–647 (1985)).. IL-1ra beta gene of FIG. 1 (SEQ ID NO:1) has about 59.0% identity (using BESTFIT (part of the GCG suite of programs)) in 230 nucleotide residues with human IL-1ra [S. P. Eisenberg et al., Nature 343:341–346, 1990].

One polynucleotide of the present invention encoding IL-1ra beta may be obtained using standard cloning and screening, from a cDNA library derived from mRNA in cells of human keratinocytes and TNFα plus IFN γ (Interferon γ) induced epithelial cells using the expressed sequence tag (EST) analysis (Adams, M. D., et al. Science (1991) 252:1651–1656; Adams, M. D. et al., Nature, (1992) 355:632–634; Adams, M. D., et al., Nature (1995) 377 supp:3–174). Polynucleotides of the invention can also be obtained from natural sources such as genomic DNA libraries or can be synthesized using well known and commercially available techniques.

Thus, the nucleotide sequence encoding IL-1ra beta polypeptides may be identical over its entire length to the coding sequence in FIG. 1 (SEQ ID NO:1), or may be a degenerate form of this nucleotide sequence encoding the polypeptide of SEQ ID NO:2, or may be highly identical to a nucleotide sequence that encodes the polypeptide of SEQ ID NO:2. Preferably, the polynucleotides of the invention contain a nucleotide sequence that is highly identical, at least identical, with a nucleotide sequence encoding a IL-1ra beta polypeptide, or at least 80% identical with the encoding nucleotide sequence set forth in FIG. 1 (SEQ ID NO:1), or at least 80% identical to a nucleotide sequence encoding the polypeptide of SEQ ID NO:2.

When the polynucleotides of the invention are used for the recombinant production of IL-1ra beta polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., Proc Natl Acad Sci USA (1989) 86:821–824, or is an HA tag. The polynucleotide may also contain non-coding, 5' and 3' sequences, such as transcribed, non-translated sequences, splicing and polyadenylation signals, ribosome binding sites and sequences that stabilize mRNA.

Among particularly preferred embodiments of the invention are polynucleotides encoding IL-1ra beta polypeptides having the amino acid sequence of set out in FIG. 1 (SEQ ID NO:2) and variants thereof.

Further preferred embodiments are polynucleotides encoding IL-1ra beta variants that have the amino acid sequence of the IL-1ra beta polypeptide of FIG. 1 (SEQ ID NO:2) in which several, 5–10, 1–5, 1–3, 1–2 or 1 amino acid residues are substituted, deleted or added, in any combination.

Further preferred embodiments of the invention are polynucleotides that are at least 80% identical over their entire length to a polynucleotide encoding the IL-1ra beta polypeptide having the amino acid sequence set out in FIG. 1 (SEQ ID NO:2), and polynucleotides which are complementary to such polynucleotides. In this regard, polynucleotides at least 80% identical over their entire length to the same are particularly preferred, and those with at least 90% are especially preferred. Furthermore, those with at least 97% are highly preferred and those with at least 98–99% are most highly preferred, with at least 99% being the most preferred.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

Polynucleotides of the invention, which are sufficiently identical to a nucleotide sequence contained in SEQ ID NO:1, may be used as hybridization probes for cDNA and genomic DNA, to isolate full-length cDNAs and genomic clones encoding IL-1ra beta polypeptide and to isolate cDNA and genomic clones of other genes that have a high sequence similarity to the IL-1ra beta gene. Such hybridization techniques are known to those of skill in the art. Typically these nucleotide sequences are 70% identical, preferably 80% identical, more preferably 90% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli, Streptomyces* and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the IL-1ra beta polypeptide is to be expressed for use in screening assays, the polypeptide may be produced at the surface of the cell. In this event, the cells may be harvested prior to use in the screening assay. If IL-1ra beta polypeptide is secreted into the medium, the medium can be recovered in order to recover and purify the polypeptide; if produced intracellularly, the cells must first be lysed before the polypeptide is recovered. IL-1ra beta polypeptides can be recovered and purified from recombinant cell cultures by well-known methods including ammonium sulfate or ethanol precipitation, acid extraction, anion or cation exchange chromatography, phosphocellulose chromatography, hydrophobic interation chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of IL-1ra beta polynucleotides for use as diagnostic reagents. Detection of a mutated form of IL-1ra beta gene associated with a dysfunction will provide a diagnostic tool that can add to or define a diagnosis of a disease or susceptibility to a disease which results from under-expression, over-expression or altered expression of IL-1ra beta. Individuals carrying mutations in the IL-1ra beta gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled IL-1ra beta nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85: 4397–4401. In another embodiment, an array of oligonucleotides probes comprising fragments from IL-1ra beta nucleotide sequences can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., Science, Vol 274, pp 610–613 (1996)).

The diagnostic assays offer a process for diagnosing or determining a susceptibility to chronic and acute inflammation, septicemia, arthritis, inflammatory bowel disease, graft vs. host disease, autoimmunity, stroke, cardiac ischemia, acute respiratory disease syndrome (ARDS), psoriasis, restenosis, traumatic brain injury, AIDS, cachexia, allergy, parasite infection, allergic rhinitis, allergic asthma, atopic dermatitis, allergic inflammatory diseases, and delayed hypersensitivity through detection of mutation in the IL-1ra beta gene by the methods described.

In addition, chronic and acute inflammation, septicemia, arthritis, inflammatory bowel disease, graft vs. host disease, autoimmunity, stroke, cardiac ischemia, acute respiratory disease syndrome (ARDS), psoriasis, restenosis, traumatic brain injury, AIDS, cachexia, allergy, parasite infection, allergic rhinitis, allergic asthma, atopic dermatitis, allergic inflammatory diseases, and delayed hypersensitivity can be diagnosed by methods comprising determining from a sample derived from a subject an abnormally decreased or increased level of IL-1ra beta polypeptide or IL-1ra beta mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an IL-1ra beta polypeptide, in a sample derived from a host are well-known to those of skill in the art. Such assay methods include radioimmunoassays, competitive-binding assays, Western Blot analysis and ELISA assays.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

The IL-1ra beta gene was mapped to chromosome 2, in a region close to IL-1α, β and IL-1ra by comparing with public databases containing sequences obtained from mapped fragments of genomic DNA obtained by PCR using synthetic oligonucleotide primer pairs.

The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the IL-1ra beta polypeptides. The term "immunospecific" means that the antibodies have substantial greater affinity for the polypeptides of the invention than their affinity for other related polypeptides in the prior art.

Antibodies generated against the IL-1ra beta polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against IL-1ra beta polypeptides may also be employed to treat chronic and acute inflammation, septicemia, arthritis, inflammatory bowel disease, graft vs. host disease, autoimmunity, stroke, cardiac ischemia, acute respiratory disease syndrome (ARDS), psoriasis, restenosis, traumatic brain injury, ADS, cachexia, allergy, parasite infection, allergic rhinitis, allergic asthma, atopic dermatitis, allergic inflammatory diseases, and delayed hypersensitivity., among others.

Vaccines

Another aspect of the invention relates to a method for inducing an immunological response in a mammal which comprises inoculating the mammal with IL-1ra beta polypeptide, or a fragment thereof, adequate to produce antibody and/or T cell immune response to protect said animal from chronic and acute inflammation, septicemia, arthritis, inflammatory bowel disease, graft vs. host disease, autoimmunity, stroke, cardiac ischemia, acute respiratory disease syndrome (ARDS), psoriasis, restenosis, traumatic brain injury, AIDS, cachexia, allergy, parasite infection, allergic rhinitis, allergic asthma, atopic dermatitis, allergic inflammatory diseases, and delayed hypersensitivity., among others. Yet another aspect of the invention relates to a method of inducing immunological response in a mammal which comprises, delivering IL-1ra beta gene via a vector directing expression of IL-1ra beta polypeptide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a IL-1ra beta polypeptide wherein the composition comprises a IL-1ra beta polypeptide or IL-1ra beta gene. The vaccine formulation may further comprise a suitable carrier. Since IL-1ra beta polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation isotonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The IL-1ra beta polypeptide of the present invention may be employed in a screening process for compounds which stimulate (agonists) or inhibit (antagonists, or otherwise called inhibitors) the synthesis or action of the IL-1ra beta polypeptide of the present invention. The IL-1ra beta polypeptide of the present invention may also be employed in a screening process for compounds which mimic the agonist or antagonist properties of the IL-1ra beta polypeptide of the present invention. Thus, polypeptides of the invention may also be used to assess and identify agonist or antagonists from, for example, cells, cell-free preparations, chemical libraries, and natural product mixtures. These agonists or antagonists may be natural substrates, ligands, receptors, etc., as the case may be, of the polypeptide of the present invention; or may be structural or functional mimetics of the polypeptide of the present invention. See Coligan et al., *Current Protocols in Immunology* 1(2):Chapter 5 (1991).

IL-1ra beta proteins are ubiquitous in the mammalian host and are responsible for many biological functions, including many pathologies. Accordingly, it is desirous to find compounds and drugs which stimulate IL-1ra beta polypeptide on the one hand and which can inhibit the function of IL-1ra beta polypeptide on the other hand. In general, agonists are employed for therapeutic and prophylactic purposes for such conditions as chronic and acute inflammation, septicemia, arthritis, inflammatory bowel disease, graft vs. host disease, autoimmunity, stroke, cardiac ischemia, acute respiratory disease syndrome (ARDS), psoriasis, restenosis, traumatic brain injury, AIDS, cachexia, allergy, parasite infection, allergic rhinitis, allergic asthma, atopic dermatitis, allergic inflammatory diseases, and delayed hypersensitivity.. Antagonists may be employed for a variety of therapeutic and prophylactic purposes for such conditions as chronic and acute inflammation, septicemia, arthritis, inflammatory bowel disease, graft vs. host disease, autoimmunity, stroke, shock, atherschlerosis, cardiac ischemia, acute respiratory disease syndrome (ARDS), psoriasis, restenosis, traumatic brain injury, ADS, cachexia, allergy, parasite infection, allergic rhinitis, allergic asthma, atopic dermatitis, allergic inflammatory diseases, and delayed hypersensitivity.

In general, such screening procedures may involve identifying, generating and using appropriate cells which express the receptor of the IL-1ra beta polypeptide of the present invention on the surface thereof. Such cells include cells from mammals, yeast, Drosophila or *E. coli*. Such cells may be identified, for example, by direct binding methods using radiolabeled or fluorescently tagged IL-1ra beta polypeptide. Cells expressing the IL-1ra beta polypeptide receptor (or cell membrane containing the expressed polypeptide) are then contacted with a test compound to observe binding, or stimulation or inhibition of a functional response. Alternatively, the cDNA for the IL-1ra beta polypeptide receptor may be cloned by the above direct binding methods using expression cloning or purification methods known in the art, and its extracellular domain expressed as a secreted or membrane protein. The soluble or membrane bound receptor can then be used to identify agonists or antagonists via direct binding methods.

The assays may simply test binding of a candidate compound wherein adherence to the cells bearing the IL-1ra beta polypeptide receptor is detected by means of a label directly or indirectly associated with the candidate compound or in an assay involving competition with a labeled IL-1ra beta polypeptide. Further, these assays may test whether the candidate compound results in a signal similar to that generated by binding of the IL-1ra beta polypeptide, using detection systems appropriate to the cells bearing the IL-1ra beta polypeptide receptor at their surfaces. Inhibitors of activation are generally assayed in the presence of a known agonist and the effect on activation by the agonist by the presence of the candidate compound is observed. Standard methods for conducting such screening assays are well understood in the art.

Examples of potential IL-1ra beta polypeptide antagonists include antibodies or, in some cases, oligonucleotides or proteins which are closely related to the ligands, substrates, receptors, etc., as the case may be, of the IL-1ra beta polypeptide, e.g., a fragment of the ligands, substrates, receptors, or small molecules which bind to the target receptor of the present invention but do not elicit a response, so that the activity of the polypeptide is prevented.

Prophylactic and Therapeutic Methods

This invention provides methods of treating an abnormal conditions related to both an excess of and insufficient amounts of IL-1ra beta polypeptide activity.

If the activity of IL-1ra beta polypeptide is in excess, several approaches are available. One approach comprises administering to a subject an inhibitor compound (antagonist) as herein above described along with a pharmaceutically acceptable carrier in an amount effective to inhibit activation by blocking binding of the IL-1ra beta polypeptide to its target receptor, or by inhibiting a second signal, and thereby alleviating the abnormal condition.

In another approach, soluble forms of IL-1ra beta polypeptides capable of binding its receptor in competition with endogenous IL-1ra beta polypeptide may be administered. Typical embodiments of such competitors comprise fragments of the IL-1ra beta polypeptide.

In still another approach, expression of the gene encoding endogenous IL-1ra beta polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456;

Dervan et al., *Science* (1991) 251:1360. These oligomers can be administered per se or the relevant oligomers can be expressed in vivo.

For treating abnormal conditions related to an under-expression of IL-1ra beta and its activity, several approaches are also available. One approach comprises administering to a subject a therapeutically effective amount of the IL-1ra beta polypeptide or a compound, i.e., an agonist or mimetic as described above, in combination with a pharmaceutically acceptable carrier, to thereby alleviate the abnormal condition. Alternatively, gene therapy may be employed to effect the endogenous production of IL-1ra beta by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996).

Formulation and Administration

Peptides, such as the soluble form of IL-1ra beta polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 μg/kg of subject. Wide variations in the needed dosage, however, are to be expected in view of the variety of compounds available and the differing efficiencies of various routes of administration. For example, oral administration would be expected to require higher dosages than administration by intravenous injection.

Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Example 1

Isolation and Identification of IL-1RAβ

A potential full length clone (HGS EST #1506331; Project ID HAICQ62 ) was initially identified through a search of the Human Genome Sciences EST database (vide supra for EST analysis) for proteins with homology to members of the interleukin 1 family. This partial sequence showed significant sequence identity (35% over 77 aa) to murine IL-1ra. This cDNA was completely sequenced on both strands using an automated sequencer. A total of 1183 bp were sequenced, and this includes an open reading frame encoding a peptide of 169 aa. The cDNA and protein sequences are SEQ ID NOS: 1 and 2, respectively, and are named IL-1raβ. The protein does not appear to have a signal sequence at its amino terminus and is likely to be expressed as an intracellular, cytosolic protein like other members of the family. It is possible that alternative splice forms exist which include a signal sequence, as has been found for IL-1ra.

The IL-1ra beta gene was mapped to chromosome 2, in a region close to IL-1α, β and IL-1ra by comparing with public databases containing sequences obtained from mapped fragments of genomic DNA obtained by PCR using synthetic oligonucleotide primer pairs. Using the algorithm BLAST, a match was found with human STS CHLC.GAAT11C03.P3330 clone GAAT11C03 (Accession number G9420 11) which can be mapped to chromosome 2 approximately 142 cM from the top of the chromosome.

Example 2

IL-1ra beta was expressed in *E. coli* in a pET15 vector (Novagen) with an amino-terminal $His_6$ tail followed by a proteolytic cleavage site for thrombin. After purification and cleavage with thrombin, the amino terminus was identical to that expected for the mammalian expressed protein. IL-1ra beta was shown to have a similar β-strand-like structure to IL-1ra based on the very similar circular dichroism spectrum. Purified IL-1ra beta (0.01–1000 ng/ml, (0.56 pM-56 nM)) was evaluated for its ability to induce interleukin-4 (IL-4) in human peripheral blood lymphocytes over 24,72 and 96 hr as measured by a commercial ELISA kit for IL-4. Several stimuli (e.g. 30 μg/ml PMA+10 ng/ml PMA; 1 μM A23187+10 ng/ml PMA; anti-CD3+anti—CD28 monoclonal antibodies; 6 nM IL-1β) were also added as positive controls. Unstimulated cells produced ~40 pg/ml IL-4 at all time points evaluated. In all cases the various stimuli above produced IL-4 which was at the highest or maximal level by 96 hr. IL-1ra beta concentration-dependently induced the formation of IL-4 to levels comparable to the other stimuli (ie up to 500 pg/ml). The induction of IL-4 is associated with TH2 responses and implicated in allergy and asthma.

What is claimed is:

1. A method for the treatment of allergy, allergic rhinitis or allergic asthma comprising administering to a subject a therapeutically effective amount of the polypeptide set forth in SEQ ID NO: 2.

* * * * *

SEQUENCE LISTING

<160> NUMBER OF SEQ ID NOS: 2

<210> SEQ ID NO 1
<211> LENGTH: 1183
<212> TYPE: DNA
<213> ORGANISM: HOMO SAPIENS

<400> SEQUENCE: 1

```
ggcacgagcc acgattcagt ccctggact gtagataaag acctttctt gccaggtgct      60
gagacaacca cactatgaga ggcactccag gagacgctga tggtggagga agggccgtct   120
atcaatcaat gtgtaaacct attactggga ctattaatga tttgaatcag caagtgtgga   180
cccttcaggg tcagaacctt gtggcagttc acgaagtga cagtgtgacc ccagtcactg    240
ttgctgttat cacatgcaag tatccagagg ctcttgagca aggcagaggg gatcccattt   300
atttgggaat ccagaatcca gaaatgtgtt tgtattgtga gaaggttgga gaacagccca   360
cattgcagct aaaagagcag aagatcatgg atctgtatgg ccaacccgag cccgtgaaac   420
ccttcctttt ctaccgtgcc aagactggta ggacctccac ccttgagtct gtggccttcc   480
cggactggtt cattgcctcc tccaagagag accagcccat cattctgact tcagaacttg   540
ggaagtcata caacactgcc tttgaattaa atataaatga ctgaactcag cctagaggtg   600
gcagcttggt ctttgtctta aagtttctgg ttcccaatgt gttttcgtct acattttctt   660
agtgtcattt tcacgctggt gctgagacag gggcaaggct gctgttatca tctcatttta   720
taatgaagaa gaagcaatta cttcatagca actgaagaac aggatgtggc ctcagaagca   780
ggagagctgg gtggtataag gctgtcctct caagctggtg ctgtgtaggc acaaggcat    840
ctgcatgagt gactttaaga ctcaaagacc aaacactgag ctttcttcta ggggtgggta   900
tgaagatgct tcagagctca tgcgcgttac ccacgatggc atgactagca cagagctgat   960
ctctgtttct gttttgcttt attccctctt gggatgatat catccagtct ttatatgttg  1020
ccaatatacc tcattgtgtg taatagaacc ttcttagcat taagaccttg taaacaaaaa  1080
taattcttgt gttaagttaa atcattttg tcctaattgt aatgtgtaat cttaaagtta   1140
aataaacttt gtgtatttat ataataaaaa aaaaaaaaa aaa                    1183
```

<210> SEQ ID NO 2
<211> LENGTH: 169
<212> TYPE: PRT
<213> ORGANISM: HOMO SAPIENS

<400> SEQUENCE: 2

```
Met Arg Gly Thr Pro Gly Asp Ala Asp Gly Gly Arg Ala Val Tyr
1               5                   10                  15

Gln Ser Met Cys Lys Pro Ile Thr Gly Thr Ile Asn Asp Leu Asn Gln
                20                  25                  30

Gln Val Trp Thr Leu Gln Gly Gln Asn Leu Val Ala Val Pro Arg Ser
            35                  40                  45

Asp Ser Val Thr Pro Val Thr Val Ala Val Ile Thr Cys Lys Tyr Pro
        50                  55                  60

Glu Ala Leu Glu Gln Gly Arg Gly Asp Pro Ile Tyr Leu Gly Ile Gln
65                  70                  75                  80
```

-continued

```
Asn Pro Glu Met Cys Leu Tyr Cys Glu Lys Val Gly Glu Gln Pro Thr
                 85                  90                  95

Leu Gln Leu Lys Glu Gln Lys Ile Met Asp Leu Tyr Gly Gln Pro Glu
            100                 105                 110

Pro Val Lys Pro Phe Leu Phe Tyr Arg Ala Lys Thr Gly Arg Thr Ser
        115                 120                 125

Thr Leu Glu Ser Val Ala Phe Pro Asp Trp Phe Ile Ala Ser Ser Lys
    130                 135                 140

Arg Asp Gln Pro Ile Ile Leu Thr Ser Glu Leu Gly Lys Ser Tyr Asn
145                 150                 155                 160

Thr Ala Phe Glu Leu Asn Ile Asn Asp
                165
```